(12) United States Patent
Higgins et al.

(10) Patent No.: US 9,928,622 B2
(45) Date of Patent: Mar. 27, 2018

(54) TIMELINE DISPLAY TOOL

(75) Inventors: Stewart Anderson Higgins, Eindhoven (NL); Alexander Adrianus Martinus Verbeek, Den Bosch (NL); Eric Christiaan Sluiters, Utrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 518 days.

(21) Appl. No.: 14/122,282

(22) PCT Filed: May 22, 2012

(86) PCT No.: PCT/IB2012/052548
§ 371 (c)(1),
(2), (4) Date: Nov. 26, 2013

(87) PCT Pub. No.: WO2012/164434
PCT Pub. Date: Dec. 6, 2012

(65) Prior Publication Data
US 2014/0092095 A1 Apr. 3, 2014

(30) Foreign Application Priority Data
Jun. 1, 2011 (EP) .................................. 11168450

(51) Int. Cl.
*G06T 11/20* (2006.01)
*G06F 3/0484* (2013.01)
(Continued)

(52) U.S. Cl.
CPC .......... *G06T 11/206* (2013.01); *G06F 3/0481* (2013.01); *G06F 3/0482* (2013.01);
(Continued)

(58) Field of Classification Search
CPC .... G06F 3/0481; G06F 3/0484; G06F 3/0482; G06F 3/0486; G06F 17/30581;
(Continued)

(56) References Cited

U.S. PATENT DOCUMENTS

| | | | |
|---|---|---|---|
| 7,890,498 B1 * | 2/2011 | Hafey et al. .................. | 707/722 |
| 7,944,445 B1 * | 5/2011 | Schorr et al. ................ | 345/440 |
| 8,391,161 B1 * | 3/2013 | Poon et al. ................... | 370/242 |
| 8,726,153 B2 | 5/2014 | Noda et al. | |
| 8,928,606 B1 * | 1/2015 | Khafizova ..................... | 345/173 |
| 2005/0144038 A1 * | 6/2005 | Tamblyn et al. ................ | 705/2 |
| 2006/0206512 A1 * | 9/2006 | Hanrahan et al. ............ | 707/102 |
| 2008/0086332 A1 | 4/2008 | Hertel et al. | |
| 2008/0086333 A1 * | 4/2008 | Hertel et al. ...................... | 705/2 |
| 2008/0086334 A1 | 4/2008 | Hertel et al. | |
| 2008/0114808 A1 * | 5/2008 | Morita et al. .............. | 707/104.1 |
| 2008/0208624 A1 | 8/2008 | Morita et al. | |
| 2008/0235277 A1 * | 9/2008 | Mathew et al. ........... | 707/104.1 |

(Continued)

FOREIGN PATENT DOCUMENTS

| | | |
|---|---|---|
| JP | 2009238136 A | 10/2009 |
| WO | 2002041134 A1 | 4/2002 |

OTHER PUBLICATIONS

Klimov, D. et al. Intelligent visualization and exploration of time-oriented data of multiple patients, Artificial Intelligence in Medicine 49 (2010) 11-31.

(Continued)

*Primary Examiner* — Jin-Cheng Wang

(57) ABSTRACT

A system for displaying time-based events on a time line is described. A first timeline unit (1) displays a first timeline showing a first plurality of events within a first time segment (3) bounded by a first begin time and a first end time. A second timeline unit (2) displays a second timeline showing a second plurality of events within a second time segment (4) bounded by a second begin time and a second end time, wherein the first timeline and the second timeline are displayed in the same scale. An interaction unit (5) enables a user to indicate a change to the displayed time segments (3, 4). A time segment updater (6) determines an updated first time segment (3) and an updated second time segment (4) based on the indicated change, keeping the scale of the first timeline equal to the scale of the second timeline, and keeping an offset between the first time segment (3) and the second time segment (4) constant. The timeline units (1, 2) are arranged for updating their respective displays according to the updated time segments (3, 4).

20 Claims, 3 Drawing Sheets

(51) Int. Cl.
*G06F 3/0481* (2013.01)
*G06F 3/0486* (2013.01)
*G06F 3/0482* (2013.01)
*G06F 19/00* (2018.01)
*G06F 17/30* (2006.01)
*G06F 11/20* (2006.01)

(52) U.S. Cl.
CPC .......... *G06F 3/0484* (2013.01); *G06F 3/0486* (2013.01); *G06F 19/322* (2013.01); *G06F 11/2058* (2013.01); *G06F 17/30581* (2013.01); *G06F 19/3487* (2013.01)

(58) Field of Classification Search
CPC ............. G06F 11/2058; G06F 11/2069; G06F 11/3082; G06F 17/30575; G06Q 30/2055; G06Q 10/06311; G06Q 10/109; G06Q 10/1097; G06Q 30/0252; G06Q 10/10; G06Q 50/22; G06Q 50/24; A61N 1/37247
USPC ....... 345/440, 157, 173, 473; 705/2, 3, 7.19; 715/702, 835
See application file for complete search history.

(56) References Cited

U.S. PATENT DOCUMENTS

2008/0288023 A1\* 11/2008 John ................................ 607/59
2009/0192823 A1\* 7/2009 Hawkins et al. ................ 705/3
2010/0057513 A1\* 3/2010 Carlson ............................ 705/8
2011/0298804 A1\* 12/2011 Hao et al. ..................... 345/440
2013/0275153 A1\* 10/2013 Dastmalchi et al. ............. 705/3

OTHER PUBLICATIONS

Fails, J.A. et al. "A Visual Interface for Multivariate Temporal Data: Finding Patterns of Events across Multiple Histories", Symposium on Visual Analytics Science and Technology, Jan. 2006.

\* cited by examiner

US 9,928,622 B2

TIMELINE DISPLAY TOOL

This application is a national stage application under 35 U.S.C. § 371 of International Application No. PCT/IB2012/052548 filed on May 22, 2012 and published in the English language on Dec. 6, 2012 as International Publication No. WO/2012/164434, which claims priority to European Application No. 11168450.2 filed on Jun. 1, 2011, the entire disclosures of which are incorporated herein by reference.

FIELD OF THE INVENTION

The invention relates to displaying timelines. The invention further relates to interacting with timelines.

BACKGROUND OF THE INVENTION

In data visualization systems, events may be displayed on a timeline to enable a user to get an overview of a plurality of events. On a timeline, a particular time duration is represented by a corresponding line segment. The events are positioned on the timeline according to the time associated with each event. The user of the visualization system may set the time window, or the time interval shown on the time line, to view a particular time period on the timeline canvas.

In some practical applications, for example a clinical informatics application, a user, such as a physician, could have a need to make a detailed comparison of several periods in a patient's medical history. These periods can be visualized on a timeline.

"Intelligent visualization and exploration of time-oriented data of multiple patients", by D. Klimov et al, in Artificial Intelligence in Medicine, 49 (2010) pp. 11-31, discloses an interactive, ontology-based exploration module, which enables the user to visualize raw data and abstract concepts for multiple patient records, at several levels of temporal granularity. An absolute, calendar-based timeline and a relative time line are disclosed. The relative time line is set by identifying clinically significant events which serve as a date of reference (time zero) for all patient data. The data of all patients is aligned according to the reference time point. The data values shown on the absolute timeline are quite different from the data values on the relative timeline, because all values and statistics are recalculated according to the new zero point. In the calendar-based timeline, the absolute dates or months are displayed along the timeline. In the relative timeline, the number of days or months from the reference time point are displayed along the timeline. In either case, the data for a plurality of patients are shown as a graph on a single timeline.

SUMMARY OF THE INVENTION

It would be advantageous to have an improved system for displaying time-based events on a time line. To better address this concern, a first aspect of the invention provides a system comprising a first timeline unit arranged for displaying a first timeline showing a first plurality of events within a first time segment bounded by a first begin time and a first end time;

a second timeline unit arranged for displaying a second timeline showing a second plurality of events within a second time segment bounded by a second begin time and a second end time, wherein the first timeline and the second timeline are displayed in the same scale;

an interaction unit arranged for enabling a user to indicate a change to the displayed time segments;

a time segment updater arranged for determining an updated first time segment and an updated second time segment based on the indicated change, keeping the scale of the first timeline equal to the scale of the second timeline, and keeping an offset between the first time segment and the second time segment constant; and wherein the timeline units are arranged for updating their respective displays according to the updated time segments.

The proposed system makes it easier to inspect two time intervals simultaneously, because two separate timelines are displayed that are synchronized with respect to scale and offset. These two separate timelines allow the user to clearly distinguish events belonging to the first time segment from events belonging to the second time segment. Moreover, easy navigation is facilitated, because the two time intervals may be changed by the user while the system keeps the scale of the timelines the same and keeps the offset between the two time intervals the same. This way, it becomes easy to compare two time intervals and to compare for example the occurrence of events in the first time interval with the occurrence of events in the second time interval.

The system may comprise a time point input unit arranged for enabling the user to indicate a first time point in respect of the first timeline and a second time point in respect of the second timeline, and wherein the first timeline unit and the second timeline unit are arranged for aligning the first time point on the first timeline with the second time point on the second timeline, and for keeping the time points aligned when the user makes a change to the time segments, wherein the offset corresponds to an offset between the first time point and the second time point. This makes it especially easy to compare the course of events at two different times, based on a reference time events that are synchronized by keeping them aligned between the two timelines. For example, a particular clinical event may occur two times for a patient, and the two timelines may show the course of events leading up to and/or following the first time that the clinical event occurred and the second time the clinical event occurred. The user may easily explore the timelines, for example by scaling or shifting the shown time segments, while the system keeps the two indicated time points aligned.

The first timeline unit and the second timeline unit may be arranged for displaying the two timelines parallel to each other, and wherein the first time point on the first timeline and the second time point on the second timeline, when aligned by the timeline units, define a line substantially perpendicular to a time axis of the first timeline or the second timeline. This is a particularly advantageous way of aligning the two time points, because it becomes easy to compare events around the aligned time points.

The change to the first time interval and the second time interval may comprise at least one of: a change of scale and a time shift. These operations are particularly advantageous to be performed in a synchronized way, because without synchronizing these operations between the two timelines, it becomes difficult to compare the course of events in the two shown timelines.

The first time interval may comprise a current period, and the second time interval may comprise a historical period. This allows to compare a current situation with a previous situation. This may be used to predict future events or to plan a course of action to achieve a particular purpose.

The system may comprise a data access unit arranged for accessing a representation of a plurality of events, each event having a time point associated therewith, wherein the first timeline unit is arranged for displaying a selection of the events associated with time points in the first time interval, and the second timeline unit is arranged for displaying a selection of the events associated with time points in the second time interval. This is a suitable way of selecting events for display in the timelines.

The events may relate to at least one patient, and the events may be stored in at least one patient record. This allows to use the timelines in medical applications.

The events selected for the first timeline and the events selected for the second timeline may relate to the same subject. For example, they may relate to the same patient or they may be stored in the same patient record.

The representation of the plurality of events may comprise at least a first set of events and a different second set of events. The events displayed on the first timeline may be selected from the first set of events, and the events displayed on the second timeline may be selected from the second set of events. This way, two separate sets of events may be compared, an more particularly, events in two different time segments may be shown for the two separate sets of events. This allows to compare a situation for e.g. a first patient at a first time with a situation for a second patient at a second time.

The first set of events may relate to a first subject, and the second set of events may relate to a second subject. This way, it becomes easy to compare events for different subjects.

The system may comprise an event filter arranged for generating the first and second set of events by filtering a plurality of events relating to the subject based on a first and second set of criteria, respectively. It is also possible to apply different selection criteria for the events shown in the two timelines. For example, the historic timeline may omit some events that are not of long-term interest, whereas the current timeline may include such events. The event filter may thus be applied to select events for display on the timeline not only based on the time of the events, but also based on other properties such as type of event.

The first timeline unit and the second timeline unit may be arranged for displaying indications of the relevant absolute time along points of the first timeline and second timeline, respectively. This makes it possible to see the time that a timeline shows. The absolute time may include a date. The absolute time may also include a time-of-day.

In another aspect, the invention provides a workstation comprising a system as set forth herein. The invention may also be provided as a web application hosted on a server, for example.

In another aspect, a method of displaying time-based events on a time line is provided. The method may comprise displaying a first timeline showing a first plurality of events within a first time segment bounded by a first begin time and a first end time;

displaying a second timeline showing a second plurality of events within a second time segment bounded by a second begin time and a second end time, wherein the first timeline and the second timeline are displayed in the same scale;

enabling a user to indicate a change to the displayed time segments;

determining an updated first time segment and an updated second time segment based on the indicated change, keeping the scale of the first timeline equal to the scale of the second timeline, and keeping an offset between the first time segment and the second time segment constant; and updating the displayed timelines according to the updated time segments.

In another aspect, the invention provides a computer program product comprising instructions for causing a processor system to perform a method set forth herein.

It will be appreciated by those skilled in the art that two or more of the above-mentioned embodiments, implementations, and/or aspects of the invention may be combined in any way deemed useful.

Modifications and variations of the workstation, the system, the method, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from and will be elucidated with reference to the embodiments described hereinafter. In the figures, similar items have been denoted with the same reference numerals.

DETAILED DESCRIPTION OF EMBODIMENTS

Figure 1A:
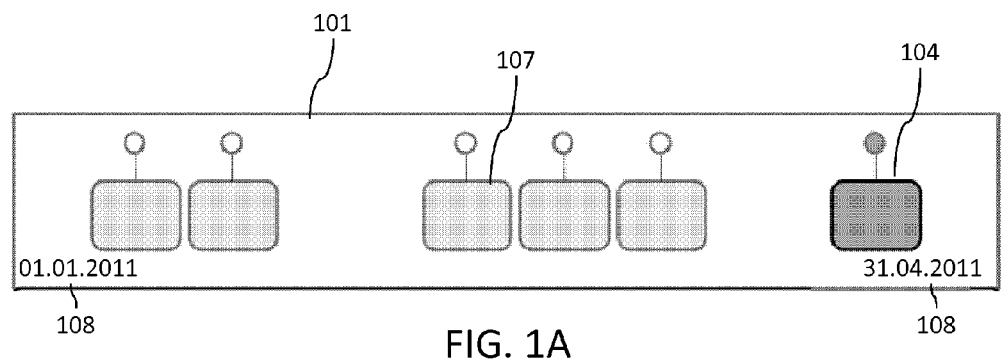
FIG. 1A is a schematic representation of a timeline.

In this description, the invention will be explained with more detail. The details mentioned herein are intended merely as examples. Modifications and alternative implementation possibilities are within reach of the person skilled in the art in view of this description.

In a clinical informatics application, a physician may want to make a detailed comparison of several periods in a patient's medical history which are accessible via a timeline. Such a comparison may be needed in cancer diagnosis and treatment planning, for example.

A patient's medical history may be represented in a timeline. The physician sets the time window shown on the timeline (start/end period) to optimally view a specific period on the timeline canvas.

Physicians may use a timeline to be informed about the patient history and to plan future care. Sometimes, the physician may want to compare two or more periods in the same patient's history. A typical example would be where a patient previously had a similar medical situation to the current one and the physician may want to find the equivalent point in the patient history to that in the current situation. The physician may want to compare the lead up to the equivalent point in the history with what has happened recently. The physician may want to plan future care, influenced by the knowledge of what care was given to the patient in the similar situation in the history.

Additionally, the same mechanism can be used to compare the medical history of two different patients, for similar reasons. Also other, non-medical sets of events may be compared, for example internal events that occur in a computer system's operating system may be analyzed on two timelines to compare particular behaviors of the system.

A physician who is interested in a specific period of a patient's medical history may manipulate the time window of the patient's clinical time-line, so that the period of interest is optimally visible on the timeline canvas. To see other periods of interest in the same detail, the user may perform a similar manipulation of the timescale and time window. This often means that the recent period of interest is not visible at the same time. When a physician wants to compare two or more clinical care periods from a patient's medical history, which can be far apart in time, it is difficult to see both in the necessary detail. Zooming out to a longer time period allows both periods of interest to be seen, but at the expense of less detail, and it is still difficult to compare because the periods are on the same timeline with other information between them.

To improve this situation, the physician may be enabled to indicate to the system that he would like to compare a historical period with the current period. A use-case (based on comparing two periods of interest) is as follows:

The user sets the current period of interest.

The user indicates to the system that he wishes to compare a period of interest in the patient history with the current period of interest.

The system retains the current timeline display settings, but makes a copy of the timeline, so that there are now two timelines—ideally above each other but they could also be side-by-side. For example, two horizontal timelines may be displayed one above the other. Alternatively, two vertical timelines may be displayed one to the left of the other. The two timelines may have the same timescale, for example, both could cover a period of 1 year or 3 months or whatever the initial scale was.

The user may navigate on the copy of the timeline to the period of interest in the patient history, for example using mouse drag and drop operations, to 'shift' the timeline in order to view a different time segment.

The user may indicate that he wants to link two time points of interest (one in the history timeline and one in the current situation timeline). The points may correspond to a folder on the timeline, such as a tumor board report or an imaging examination. However, this is not a limitation.

The user may indicate the two points of interest and the application may be arranged for vertically aligning the two timelines through these two points. This defines an offset between two timelines with the same scale on both timelines.

Now, when the user changes the time window or moves backwards and forwards on the timeline, both timelines follow, and the points of interest remain aligned and therefore the defined offset is maintained. Also, when the user changes the scale, both timelines are updated to the new scale, and the defined offset is maintained.

The user is thus able to easily compare the two periods of interest. When no longer needed the user may indicate that he or she wishes to leave the compare mode. In this case, the timeline with the current period of interest may be maintained while the historical timeline may be removed from the display. Consequently, leaving compare mode causes the system to return to normal timeline viewing. Alternatively, both timelines are maintained, while the alignment is no longer enforced. For example, when the user changes a scale or shifts the time window, this is applied only to one of the timelines, not to both, and the offset is not maintained.

It is also possible to use specific commands that the user may employ for "synchronized adjustment" (in which scale and offset are kept the same for both timelines) and "individual adjustment" (in which scale and offset can be adjusted individually for a particular timeline). Consequently, there is no need to explicitly link and unlink the timelines.

Figure 1B:
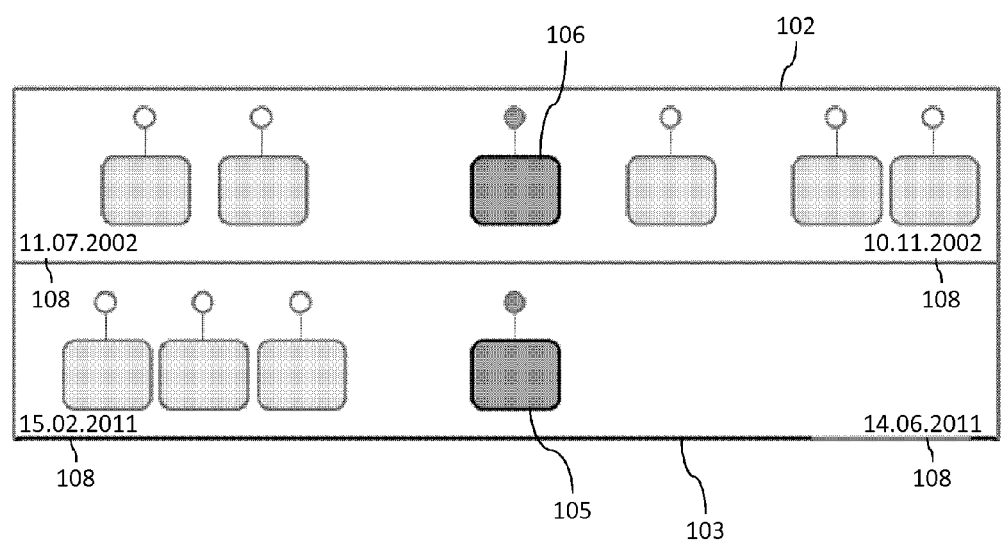
FIG. 1B is a schematic representation of two linked timelines.

FIG. 1A illustrates what the timeline 101 may look like (conceptually) before the timeline compare functionality is activated. A button may be provided in a graphical user interface (not shown), for example, to activate and/or deactivate the timeline compare functionality. Also, controls (not shown) may be provided for enabling the user to change the shown time segment. The symbols 107 represent events shown on the timeline. Date indications 108 may be provided to indicate to the user the bounds of the time segment shown. It is also possible to indicate further absolute time indications, for example at regular intervals along the timeline. It is also possible to indicate the absolute time of one or more or all of the shown events. The user may be particularly interested in events around event 104, and may wish to compare the events with a historical time period, for example. The user may indicate that he wishes to add an additional timeline. This results in two timelines, as shown in FIG. 1B. The user may navigate both timelines individually to the desired time segment. The absolute time indications 108 are updated for both timelines individually to indicate the time segment shown on the timeline. The user may then indicate that he wishes to link time points corresponding to events 105 and 106. After that, any manipulations of the time segment are performed on both timelines 102 and 103. This facilitates comparing the course of events in the two time segments shown.

Easy comparison of two or more periods of interest on a patient history time-line is thus achieved. A point in the current period of interest may be aligned with a point from the historical period of interest. This offset may be maintained in the compare mode. The timescales may also be synchronized. Interaction with both timelines may be achieved via a single navigator. In this way, the clinical user can easily compare similar periods in history with the situation of today and can get the benefit of seeing what was historically planned for the patient (and potentially the outcome)—as input to planning forward from today.

After the user has indicated the periods of interest, they may be aligned vertically through similar point of interest in each period (specified by the user).

Each period may have its own absolute start/end, but the time difference between start and end may be common to all compared periods (=so they are on the same scale).

The scale can be changed and the similar point of interest can also be moved backwards/forwards in time using one common navigator, so that the historical periods "follow" the period of today in a synchronized way (with a common time window).

The events shown on the first timeline may relate to a first sequence of events, and the events shown on the second timeline may relate to a second sequence of events. This covers also the case when events are similar but not exactly the same.

Figure 2:
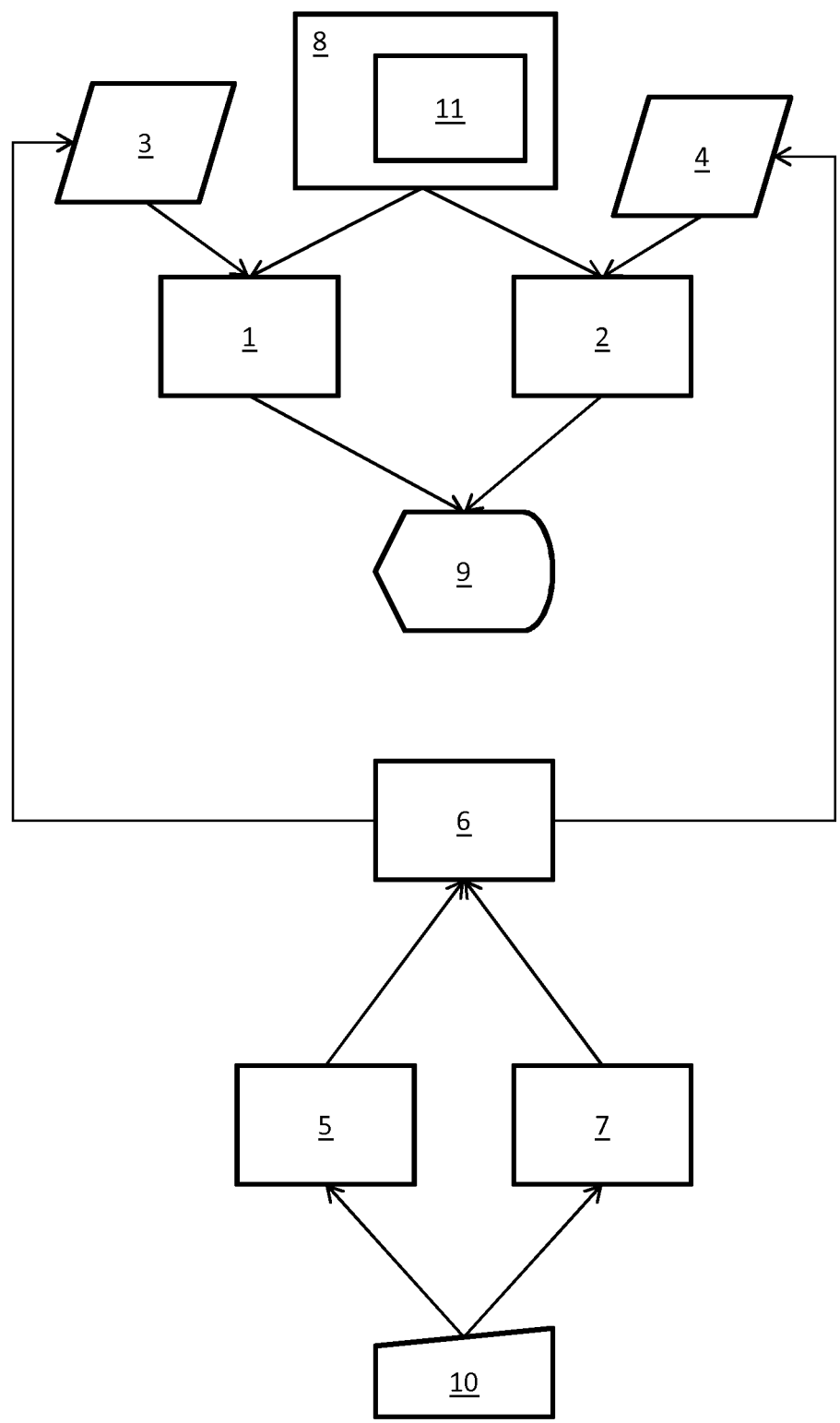
FIG. 2 is a block diagram of a system for displaying time-based events on a time line.

FIG. 2 shows a block diagram illustrating aspects of a system for displaying time-based events on a time line. The system may be implemented on computer-based hardware, using software to implement some of the features described herein. The system may be implemented on a standalone workstation, or on a distributed computer system.

The system may comprise a first timeline unit 1 for displaying a first timeline showing a first plurality of events within a first time segment 3 bounded by a first begin time and a first end time. The user may be enabled to indicate the time segment shown, or this may be performed automatically. For example, always the last x days may be shown.

The system may comprise a second timeline unit 2 for displaying a second timeline showing a second plurality of events within a second time segment 4 bounded by a second begin time and a second end time. The first and second timeline units may be instantiations of a timeline class, for example. The first timeline and the second timeline are displayed in the same scale. The timeline units 1, 2 may be arranged for displaying their timeline in the form of a bar on which the points along the bar represent points in time, so that the bar covers a contiguous time segment. An event may be displayed on the bar at the time corresponding to the event. Such an event may be displayed by means of an icon or another symbol. Alternatively, the bar may have a different color at a time point for which there is an event. The symbol or icon may also provide some information about the event, for example, different kinds of event may be displayed using a different symbol, icon, or color. Moreover, a text label may be displayed for the event. Such a text label may also represent information about the event, such as type of event or an indication of a contents of a document describing the event. Besides this event-based kind of timeline, another kind of timeline may comprise a graph wherein one of the axes represents a time axis.

The system may comprise an interaction unit 5 for enabling a user to indicate a change to the displayed time segments 3, 4. The change to the first time segment 3 and the second time segment 4 may comprise a change of scale. The change may also comprise a time shift. Other changes may also be supported by the system. Two modes of change may be supported by the system, linked mode and unlinked mode. In unlinked mode, the time segments shown may be adjusted for a timeline individually. The system may allow to adjust only the time segment of one of the timelines, or to adjust the time segments of both or all timelines. In linked mode, any adjustment of the time segment is applied to both timelines.

The system may comprise a time segment updater 6. In linked mode, for determining an updated first time segment 3 and an updated second time segment 4 based on the indicated change, the time segment updater 6 is arranged for keeping the scale of the first timeline equal to the scale of the second timeline, and keeping an offset between the first time segment 3 and the second time segment 4 constant. This offset may be computed by comparing a given time point in the time segments. For example, the lower bounds of the time segments may be compared. Alternatively, the upper bounds may be compared. Alternatively, a selected point in the time segment may be compared. The comparison may comprise computing the amount of time between the two points to determine the offset. In case of a selected point, the time segment updater may be arranged for keeping the selected point at a fixed position on the timeline. However, this is optional.

The timeline units 1, 2 may be arranged for updating their respective displays according to the updated time segments 3, 4.

The system may comprise a time point input unit 7 for enabling the user to indicate a first time point in respect of the first timeline and a second time point in respect of the second timeline. The system may restrict the user to let the user select only time points that lie within the respective time segment. However, this is not a limitation. The first timeline unit and the second timeline unit may be arranged for aligning the first time point on the first timeline with the second time point on the second timeline, and for keeping the time points aligned when the user makes a change to the time segments.

The first timeline unit 1 and the second timeline unit 2 may be arranged for displaying the two timelines parallel to each other, and wherein the first time point on the first timeline and the second time point on the second timeline, when aligned by the timeline units, define a line substantially perpendicular to a time axis of the first timeline or the second timeline. For example, when the two timelines 102 and 103 are displayed below each other, as is the case in FIG. 1, then the first time point 106 is displayed directly above the second time point 105.

For example, the first time segment 3 comprises a current period, and the second time segment 4 comprises a historical period. However, this is not a limitation. Moreover, the user may be enabled to change the time segments 3 and 4 in unlinked mode to any desired time period. In linked mode, the offset between the two time segments is kept constant.

The system may comprise a data access unit 8 for accessing a representation of a plurality of events. Each event may have a time point associated therewith. There may be events without time point, but these events are usually not displayed on the timeline. The first timeline unit 1 may be arranged for displaying a selection of the events associated with time points in the first time segment 3, and the second timeline unit 2 may be arranged for displaying a selection of the events associated with time points in the second time segment 4.

The events may relate to at least one patient, and the events may be stored in at least one patient record. However, this is not a limitation. Other kinds of events, such as events in a computer operating system, or events in public transportation time tables, may be processed by the system.

The events selected for the first timeline and the events selected for the second timeline may relate to the same subject. For example, the events of both timelines may be taken from one collection of events, and the selection may be made purely based on the times of the events. Alternatively, the representation of the plurality of events may comprise at least a first set of events and a different second set of events, and wherein the events displayed on the first timeline are selected from the first set of events, and the events displayed on the second timeline are selected from the second set of events. This allows to view different datasets in the two timelines. For example, the first set of events may relate to a first subject, and the second set of events relate to a second subject.

The system may comprise an event filter 11 arranged for generating the first and second set of events by filtering a plurality of events relating to the subject based on a first and second set of criteria, respectively. The event filter 11 may filter one large dataset to generate the first and second set, or may obtain the events for the first set and second set from different source sets.

The first timeline unit 1 and the second timeline unit 2 may be arranged for displaying indications of the relevant absolute time along points of the first timeline and second timeline, respectively. The relevant absolute time refers to the time point represented by that point of the timeline.

Figure 3:
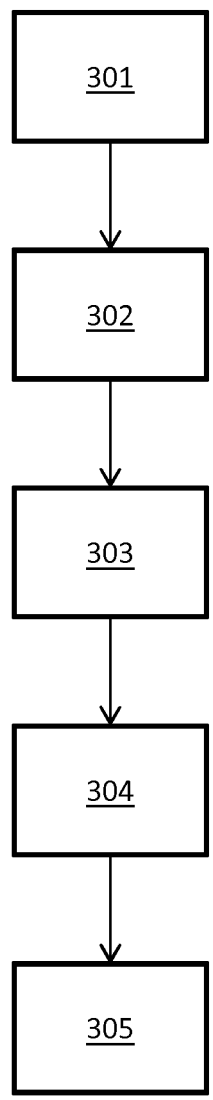
FIG. 3 is a flowchart of a method of displaying time-based events on a time line.

FIG. 3 illustrates a method of displaying time-based events on a time line. Step 301 displays a first timeline showing a first plurality of events within a first time segment bounded by a first begin time and a first end time. Step 302 displays a second timeline showing a second plurality of events within a second time segment bounded by a second begin time and a second end time, wherein the first timeline and the second timeline are displayed in the same scale. Step 303 enables a user to indicate a change to the displayed time segments. Step 304 determines an updated first time segment and an updated second time segment based on the indicated change, keeping the scale of the first timeline equal to the scale of the second timeline, and keeping an offset between the first time segment and the second time segment constant. Step 305 updates the displayed timelines according to the updated time segments. Steps 303, 304, and 305 may be repeated as often as necessary. The method may be implemented by means of a computer program.

The system and method described herein may be extended with more timelines. These timelines may be synchronized in a similar way as the two timelines described in more detail herein. For example, the scale and the offset between the time segments displayed in the three or more timelines may be kept constant when the user changes the time segment.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a flash drive or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A method for presenting multiple timeline visualizations, the method comprising
   causing a display device to display:
      a first timeline segment (FTS) extending between an FTS first start point and an FTS first end point, and
      a second timeline segment (STS) extending between an STS first start point and an STS first end point;
   receiving a first input of a first type indicating a first change to the FTS;
   causing, based on the first input, the display device to update the display of the first timeline segment to start at a FTS second start point different from the FTS first start point, wherein the FTS second start point and the STS first start point are associated with respective times that are temporally separated from each other by a first temporal offset value;
   receiving a second input of a second type indicating a second change to the STS;
   causing, based on the second input, the display device to update both
      the display of the FTS to start at a FTS third start point, and
      the display of the STS to start at a STS second start point, wherein the FTS third start point and the STS second start point are associated with respective times that remain temporally separated from each other by the first temporal offset value.

2. The method of claim 1, wherein:
the first input of the first type is a command entered while operating in an unlinked mode; and
the second input of the second type is a navigation command to shift a time window of the FTS to a new time.

3. The method of claim 1, wherein:
the step of causing the display device to display the FTS and the STS further comprises causing the display device to display a third timeline segment (TTS) extending between a TTS first start point and a TTS first end point,
the FTS second start point and the TTS first start point are associated with respective times that are temporally separated from each other by a second temporal offset value, and
the step of causing, based on the second input, the display device to update the FTS and the STS further comprises causing the display device to update the display of the TTS to start at a TTS second start point, wherein the FTS third start point and the TTS second start point are associated with respective times that remain temporally separated from each other by the second temporal offset value.

4. The method of claim 1, wherein the FTS and STS are segments of a single common timeline.

5. The method of claim 1, wherein the first input is a link command to link the FTS and the STS positions with the first temporal offset.

6. The method of claim 1, wherein the first input comprises a selection of a first symbol from the FTS and a second symbol from the STS, wherein the first symbol and second symbol are associated with respective times that are temporally separated from each other by the first temporal offset.

7. The method of claim 1, wherein the second input of the second type is a navigation command to shift a time window of the FTS to a new time.

8. A non-transitory machine-readable medium encoded with instructions for execution by a processor for presenting multiple timeline visualizations, the non-transitory machine-readable medium comprising
  instructions for causing a display device to display:
    a first timeline segment (FTS) extending between an FTS first start point and an FTS first end point, and a second timeline segment (STS) extending between an STS first start point and an STS first end point;
  instructions for receiving a first input of a first type indicating a first change to the FTS;
  instructions for causing, based on the first input, the display device to update the display of the first timeline segment to start at a FTS second start point different from the FTS first start point, wherein the FTS second start point and the STS first start point are associated with respective times that are temporally separated from each other by a first temporal offset value;
  instructions for receiving a second input of a second type indicating a second change to the STS;
  instructions for causing, based on the second input, the display device to update both
    the display of the FTS to start at a FTS third start point, and
    the display of the STS to start at a STS second start point, wherein the FTS third start point and the STS second start point are associated with respective times that remain temporally separated from each other by the first temporal offset value.

9. The non-transitory machine-readable medium of claim 8, wherein:
  the first input of the first type is a command entered while operating in an unlinked mode; and
  the second input of the second type is a navigation command to shift a time window of the FTS to a new time.

10. The non-transitory machine-readable medium of claim 8, wherein:
  the instructions for causing the display device to display the FTS and the STS further comprise instructions for causing the display device to display a third timeline segment (TTS) extending between a TTS first start point and a TTS first end point,
  the FTS second start point and the TTS first start point are associated with respective times that are temporally separated from each other by a second temporal offset value, and
  the instructions for causing, based on the second input, the display device to update the FTS and the STS further comprise instructions for causing the display device to update the display of the TTS to start at a TTS second start point, wherein the FTS third start point and the TTS second start point are associated with respective times that remain temporally separated from each other by the second temporal offset value.

11. The non-transitory machine-readable medium of claim 8, wherein the FTS and STS are segments of a single common timeline.

12. The non-transitory machine-readable medium of claim 8, wherein the first input is a link command to link the FTS and the STS positions with the first temporal offset.

13. The non-transitory machine-readable medium of claim 8, wherein the first input comprises a selection of a first symbol from the FTS and a second symbol from the STS, wherein the first symbol and second symbol are associated with respective times that are temporally separated from each other by the first temporal offset.

14. The non-transitory machine-readable medium of claim 8, wherein the second input of the second type is a navigation command to shift a time window of the FTS to a new time.

15. A device for presenting multiple timeline visualizations, the device comprising
  a memory;
  a display device interface for transmitting information toward a display device; and
  a processor configured to:
    cause the display device to display:
      a first timeline segment (FTS) extending between an FTS first start point and an FTS first end point, and a second timeline segment (STS) extending between an STS first start point and an STS first end point;
    receive a first input of a first type indicating a first change to the FTS;
    cause, based on the first input, the display device to update the display of the first timeline segment to start at a FTS second start point different from the FTS first start point, wherein the FTS second start point and the STS first start point are associated with respective times that are temporally separated from each other by a first temporal offset value;
    receive a second input of a second type indicating a second change to the STS;
    cause, based on the second input, the display device to update both
      the display of the FTS to start at a FTS third start point, and
      the display of the STS to start at a STS second start point, wherein the FTS third start point and the STS second start point are associated with respective times that remain temporally separated from each other by the first temporal offset value.

16. The device of claim 15, wherein:
  the first input of the first type is a command entered while operating in an unlinked mode; and
  the second input of the second type is a navigation command to shift a time window of the FTS to a new time.

17. The device of claim 15, wherein:
  in causing the display device to display the FTS and the STS, the processor is further configured to cause the display device to display a third timeline segment (TTS) extending between a TTS first start point and a TTS first end point,
  the FTS second start point and the TTS first start point are associated with respective times that are temporally separated from each other by a second temporal offset value, and
  in causing, based on the second input, the display device to update the FTS and the STS the processor is further configured to cause the display device to update the display of the TTS to start at a TTS second start point, wherein the FTS third start point and the TTS second start point are associated with respective times that remain temporally separated from each other by the second temporal offset value.

18. The device of claim 15, wherein the first input is a link command to link the FTS and the STS positions with the first temporal offset.

19. The device of claim 15, wherein the first input comprises a selection of a first symbol from the FTS and a second symbol from the STS, wherein the first symbol and second symbol are associated with respective times that are temporally separated from each other by the first temporal offset.

20. The device of claim 15, wherein the second input of the second type is a navigation command to shift a time window of the FTS to a new time.

* * * * *